United States Patent
Kopp et al.

(10) Patent No.: US 11,596,487 B2
(45) Date of Patent: *Mar. 7, 2023

(54) ROBOTIC SURGICAL SYSTEM CONTROL SCHEME FOR MANIPULATING ROBOTIC END EFFECTORS

(71) Applicant: Covidien LP, Mansfield, MA (US)

(72) Inventors: Brock Kopp, Boulder, CO (US); Kevin R. Slisz, Old Saybrook, CT (US)

(73) Assignee: Covidien LP, Mansfield, MA (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/101,024

(22) Filed: Nov. 23, 2020

(65) Prior Publication Data

US 2021/0068910 A1    Mar. 11, 2021

Related U.S. Application Data

(63) Continuation of application No. 15/758,908, filed as application No. PCT/US2016/050359 on Sep. 6, 2016, now Pat. No. 10,849,700.

(60) Provisional application No. 62/217,492, filed on Sep. 11, 2015.

(51) Int. Cl.
| | | |
|---|---|---|
| A61B 34/35 | (2016.01) | |
| A61B 34/30 | (2016.01) | |
| A61B 17/34 | (2006.01) | |
| A61B 34/32 | (2016.01) | |
| A61B 90/00 | (2016.01) | |

(Continued)

(52) U.S. Cl.
CPC .......... *A61B 34/35* (2016.02); *A61B 17/3421* (2013.01); *A61B 34/30* (2016.02); *A61B 17/29* (2013.01); *A61B 18/1442* (2013.01); *A61B 34/32* (2016.02); *A61B 2090/061* (2016.02); *A61B 2090/0807* (2016.02)

(58) Field of Classification Search
CPC ......... A61B 34/30; A61B 34/32; A61B 34/35; A61B 34/3421
See application file for complete search history.

(56) References Cited

U.S. PATENT DOCUMENTS

| | | |
|---|---|---|
| 6,620,173 B2 | 9/2003 | Gerbi et al. |
| 10,335,182 B2 | 7/2019 | Stulen et al. |
| 10,849,700 B2 | 12/2020 | Kopp et al. |

(Continued)

FOREIGN PATENT DOCUMENTS

| | | |
|---|---|---|
| WO | 9639944 A1 | 12/1996 |
| WO | 2014127984 A1 | 8/2014 |

OTHER PUBLICATIONS

International Search Report and Written Opinion for Int'l Appln. No. PCT/US2016/050359 dated Dec. 22, 2016.

(Continued)

*Primary Examiner* — Tuan V Nguyen
(74) *Attorney, Agent, or Firm* — Carter, DeLuca & Farrell, LLP

(57) ABSTRACT

A method of controlling a robotic surgical system is provided, where the robotic surgical system including an arm having an instrument with jaws and an access port each coupled to the arm. The method includes detecting a position of the instrument, and opening the jaws of the instrument, in response to a determination that a distance between the position of the instrument and a position of the access port is greater than a predetermined distance.

9 Claims, 7 Drawing Sheets

(51) Int. Cl.
 *A61B 18/14* (2006.01)
 *A61B 17/29* (2006.01)

(56) References Cited

U.S. PATENT DOCUMENTS

| | | |
|---|---|---|
| 2008/0065111 A1* | 3/2008 | Blumenkranz ...... B25J 15/0009 |
| | | 606/130 |
| 2013/0150865 A1 | 6/2013 | Min et al. |
| 2013/0172908 A1 | 7/2013 | Sang et al. |
| 2014/0005703 A1 | 1/2014 | Stulen |
| 2014/0246479 A1 | 9/2014 | Baber et al. |

OTHER PUBLICATIONS

European Communication dated Apr. 4, 2019 (1 p) regarding Supplementary Search Report enclosing an Extended European Search Report dated Mar. 26, 2019 corresponding to couterpart Patent Application EP 16844926.2 (11 pp).
Chinese First Office Action dated Apr. 26, 2020 corresponding to counterpart Patent Application CN 201680051129.2.

\* cited by examiner

ROBOTIC SURGICAL SYSTEM CONTROL SCHEME FOR MANIPULATING ROBOTIC END EFFECTORS

CROSS-REFERENCE TO RELATED APPLICATIONS

This application is a Continuation Application which claims the benefit of and priority to U.S. patent application Ser. No. 15/758,908, filed on Mar. 9, 2018 (now U.S. Pat. No. 10,849,700), which is a U.S. National Stage Application filed under 35 U.S.C. § 371(a) of International Patent Application Ser. No. PCT/US2016/050359, filed Sep. 6, 2016, which claims the benefit of and priority to U.S. Provisional Patent Application Ser. No. 62/217,492, filed Sep. 11, 2015, the entire disclosure of which is incorporated by reference herein.

BACKGROUND

Robotic surgical systems are increasingly being used to perform minimally invasive medical procedures. Typically during such medical procedures, a patient is placed on a platform adjacent a robotic system, and a clinician is positioned at a console remote from the robotic surgical system. The clinician provides input to a user interface, such as an input controller or handle, to manipulate a tool coupled to an arm of the robotic system, for example, an end effector, that acts on the patient.

The robotic surgical system can include a tower supporting a robot arm, and at least one end effector such as forceps or a grasping tool mounted to the robot arm via a wrist assembly. In such a configuration, during the medical procedure, the end effector and the wrist assembly are inserted into a small incision (via a cannula) or a natural orifice of a patient to position the end effector at a surgical site within the body of the patient Oftentimes when the tool is removed from the surgical site within the body of the patient, the tool includes bodily fluids and/or tissue thereon. To optimize instrument performance, the bodily fluids and/or tissue are preferably removed from the tool prior to re-insertion into the patient. Although a surgical technician is typically positioned bedside and tasked with cleaning the tools, the technician will often wear protective gloves or other clothing, which though needed, may cause inefficiencies during the surgery. In particular, as the tools are increasingly being designed to improve surgical precision, the end effectors being implemented are increasingly becoming smaller and smaller in dimension, thus becoming more difficult for surgical technicians to manipulate, especially while wearing the protective gloves. Prior to removing the tool from a patient, an end effector of the tool typically passes through an access port. End effectors of these tools typically had to be aligned with the access port opening in order for the tool to be removed from the access port. For example, a pair of jaw end effectors often had to be moved to the closed position for the jaws to fit through the port opening. The closed jaws made it difficult to clean the jaws prior to reinserting the tool into the patient. There is a need for easier accessibility and cleaning of minimally invasive surgical tools during surgery.

SUMMARY

End effectors of surgical instruments coupled an arm of a robotic surgical system may be manipulated so that the instrument may be quickly and easily removed from a patient through a relatively narrow access port opening while still enabling the instrument and its end effector to be quickly cleaned prior to reinsertion into the patient. A position of the instrument, which may include a position of an instrument end effector such as a pair of jaws, may be detected relative to an instrument access port using positional, presence detection, or other sensors in the robotic system. The jaws may be electromechanically opened responsive to a determination that a distance between the instrument and the access port is greater than a predetermined distance.

The distance between the jaws of the instrument may be further increased in response to a determination that the distance between the position of the instrument and the position of the access port is increasing.

The distance between the jaws may be increased proportionally based on an interpolation of the distance between the position of the instrument relative to the position of the access port as the distance between the position of the instrument relative to the position of the access port increases.

The jaws of the instrument may be closed in response to a determination that the distance between the position of the instrument and the position of the access port is less than the predetermined distance.

The distance between the jaws may be decreased proportionally based on an interpolation of the distance between the position of the instrument relative to the position of the access port as the distance between the position of the instrument relative to the position of the access port decreases.

If the instrument is moved in a direction co-axial with the access port, the opening of the jaws of the instrument may include increasing a distance between the jaws based on an interpolation of a change in height of the instrument along the direction co-axial with the access port relative to the position of the access port.

The predetermined distance may include a range of distances and the jaws of the instrument may be maintained in a closed position, in response to a determination that the distance between the position of the instrument and a position of the access port is within the range of distances.

A robotic surgical system may include an arm, an elongated mount coupled to the arm, an instrument, a processor, and a memory. The elongated mount may have a proximal end and a distal end, and the instrument may be detachably coupled to the elongated mount and slideable between the proximal end and the distal end. The instrument may include an end effector such as jaws moveable between an open position and a closed position. The access port may in some instances be disposed on the arm proximate the distal end of the elongated mount. The processor may be communicatively coupled to the arm, the elongated mount, and the instrument. The memory may be communicatively coupled to the processor and include instructions that, when executed by the processor, causes the processor to detect a position of the instrument and open the jaws of the instrument, in response to a determination that a distance between the position of the instrument and a position of the access port is greater than a predetermined distance.

The memory may further include instructions that, when executed by the processor, causes the processor to increase a distance between the jaws of the instrument, in response to a determination that the distance between the position of the instrument and the position of the access port is increasing.

The memory may further include instructions that, when executed by the processor, causes the processor to gradually increase the distance between the jaws proportionally based on an interpolation of the distance between the position of the instrument relative to the position of the access port as the distance between the position of the instrument relative to the position of the access port increases.

The memory may further include instructions that, when executed by the processor, causes the processor to close the jaws of the instrument, in response to a determination that the distance between the position of the instrument and the position of the access port is less than the predetermined distance.

The memory may further include instructions that, when executed by the processor, causes the processor to gradually decreasing the distance between the jaws proportionally based on an interpolation of the distance between the position of the instrument relative to the position of the access port as the distance between the position of the instrument relative to the position of the access port decreases.

The memory may further include instructions that, when executed by the processor, causes the processor to open the jaws of the instrument by increasing a distance between the jaws, based on an interpolation of a position of the instrument along the elongated mount relative to the position of the access port.

The predetermined distance may include a range of distances and may maintain the jaws of the instrument in a closed position, in response to a determination that the distance between the position of the instrument and a position of the access port is within the range of distances.

A non-transitory computer-readable medium may store a computer program product including instructions for controlling a robotic surgical system including an arm having an instrument and an access port each coupled to the arm, that, when executed by a processor, are operable to detect a position of the instrument and open jaws of the instrument, in response to a determination that a distance between the position of the instrument and a position of the access port is greater than a predetermined distance.

The non-transitory computer-readable may further include instructions, when executed by the processor, to further cause an increase of a distance between the jaws of the instrument, in response to a determination that the distance between the position of the instrument and the position of the access port is increasing.

The non-transitory computer-readable may further include instructions, when executed by the processor, to further cause a gradual increase of the distance between the jaws proportionally based on an interpolation of the distance between the position of the instrument relative to the position of the access port as the distance between the position of the instrument relative to the position of the access port increases.

The non-transitory computer-readable may further include instructions, when executed by the processor, to further cause a closing of the jaws of the instrument, in response to a determination that the distance between the position of the instrument and the position of the access port is less than the predetermined distance.

The non-transitory computer-readable may further include instructions, wherein the closing of the jaws of the instrument includes gradually decreasing the distance between the jaws proportionally based on an interpolation of the distance between the position of the instrument relative to the position of the access port as the distance between the position of the instrument relative to the position of the access port decreases.

The instrument may be moveable in a direction co-axial with the access port and the non-transitory computer-readable may further include instructions, when executed by the processor, to further cause the opening of the jaws of the instrument including increasing a distance between the jaws, based on an interpolation of a height of the instrument in the direction co-axial with the access port relative to the position of the access port.

The predetermined distance may include a range of distances and may maintain the jaws of the instrument in a closed position, in response to a determination that the distance between the position of the instrument and a position of the access port is within the range of distances.

An end effector of a surgical instrument coupled to an arm of a robotic surgical system may also be manipulated by detecting, using positional, proximity detection, or other sensors, a position of the end effector relative to an instrument access port. The end effector may be electromechanically to a position that does not clear an opening of the access port responsive to the detected position of the end effector clearing the opening of the access port.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
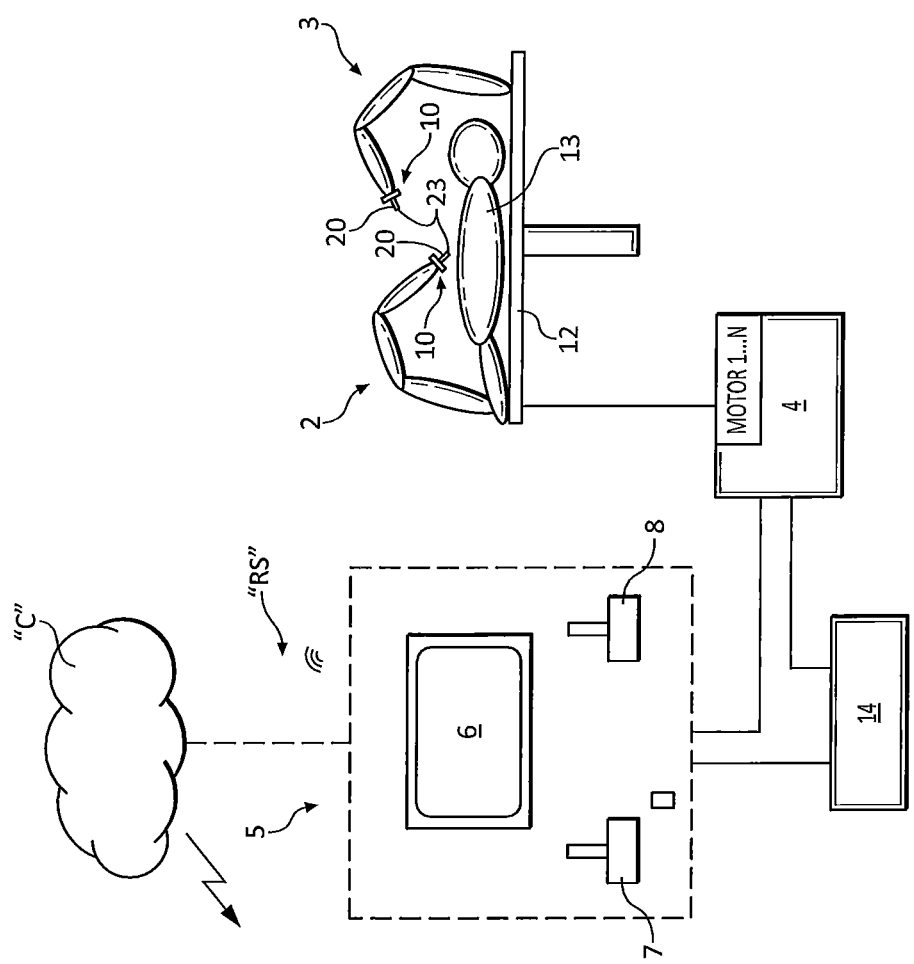
FIG. 1 is a schematic illustration of a robotic surgical system in accordance with the present disclosure.

Embodiments of the robotic surgical system and surgical assembly are described in detail with reference to the drawings, in which like reference numerals designate identical or corresponding elements in each of the several views. As used herein the term "distal" refers to that portion of the surgical assembly that is closer to the patient, while the term "proximal" refers to that portion of the surgical assembly that is farther from the patient.

With reference to FIG. 1, a robotic surgical system 1 includes a plurality of robotic arms 2, 3, a control device 4, and a console 5 coupled to the control device 4. As illustrated in FIG. 1, the surgical system 1 is configured for use on a patient 13 lying on a patient table 12 for performance of a minimally invasive surgical operation. The console 5 includes a display device 6 and input devices 7, 8. The display device 6 is set up to display three-dimensional images, and the manual input devices 7, 8 are configured to allow a clinician to telemanipulate the robotic arms 2, 3.

Each of the robotic arms 2, 3 is made up of a plurality of members connected through joints and includes a surgical assembly 10 connected to a distal end of a corresponding robotic arm 2, 3. In an embodiment, the surgical assembly 10 includes a surgical instrument 20 supporting an end effector 23. Although two robotic arms 2, 3, are depicted, the surgical system 1 may include more than two robotic arms 2, 3. In this regard, the additional robotic arms (not shown) are likewise connected to the control device 4 and are telemanipulatable via the console 5. Accordingly, one or more additional surgical assemblies 10 and/or surgical instruments 20 may also be attached to the additional robotic arm.

The robotic arms 2, 3 may be driven by electric drives (not shown) that are connected to the control device 4. According to an embodiment, the control device 4 is configured to activate drives, for example, via a computer program, such that the robotic arms 2, 3 and the surgical assemblies 10 and/or surgical instruments 20 corresponding to the robotic arms 2, 3, execute a desired movement received through the manual input devices 7, 8. The control device 4 may also be configured to regulate movement of the robotic arms 2, 3 and/or of the drives.

The control device 4 may control a plurality of motors (for example, Motor 1 . . . n) with each motor configured to drive a pushing or a pulling of one or more cables such as cables (not shown) coupled to the end effector 23 of the surgical instrument 20. In use, as these cables are pushed and/or pulled, the one or more cables effect operation and/or movement of the end effector 23. The control device 4 coordinates the activation of the various motors to coordinate a pushing or a pulling motion of one or more cables in order to coordinate an operation and/or movement of one or more end effectors 23. In an embodiment, each motor is configured to actuate a drive rod or a lever arm to effect operation and/or movement of end effectors 23 in addition to, or instead of one or more cables.

The control device 4 included any suitable logic control circuit adapted to perform calculations and/or operate according to a set of instructions. The control device 4 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of work station 1. The remote system "RS" can include any suitable electronic service, database, platform, cloud "C" (see FIG. 1), or the like. The control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, the remote system "RS."

The control device 4 can include a plurality of inputs and outputs for interfacing with the components of the work station 1, such as through a driver circuit. The control device 4 can be configured to receive input signals and/or generate output signals to control one or more of the various components (e.g., one or more motors) of the work station 1. The output signals can include, and/or can be based upon, algorithmic instructions which may be pre-programmed and/or input by a user. The control device 4 can be configured to accept a plurality of user inputs from a user interface (e.g., switches, buttons, touch screen, etc. of operating the console 5) which may be coupled to remote system "RS."

A memory 14 can be directly and/or indirectly coupled to the control device 4 to store instructions and/or databases including pre-operative data from living being(s) and/or anatomical atlas(es). The memory 14 can be part of, and/or or operatively coupled to, remote system "RS."

In accordance with an embodiment, the distal end of each robotic arm 2, 3 is configured to releasably secure the end effector 23 (or other surgical tool) therein and may be configured to receive any number of surgical tools or instruments, such as, for example, a trocar or retractor.

Figure 2:
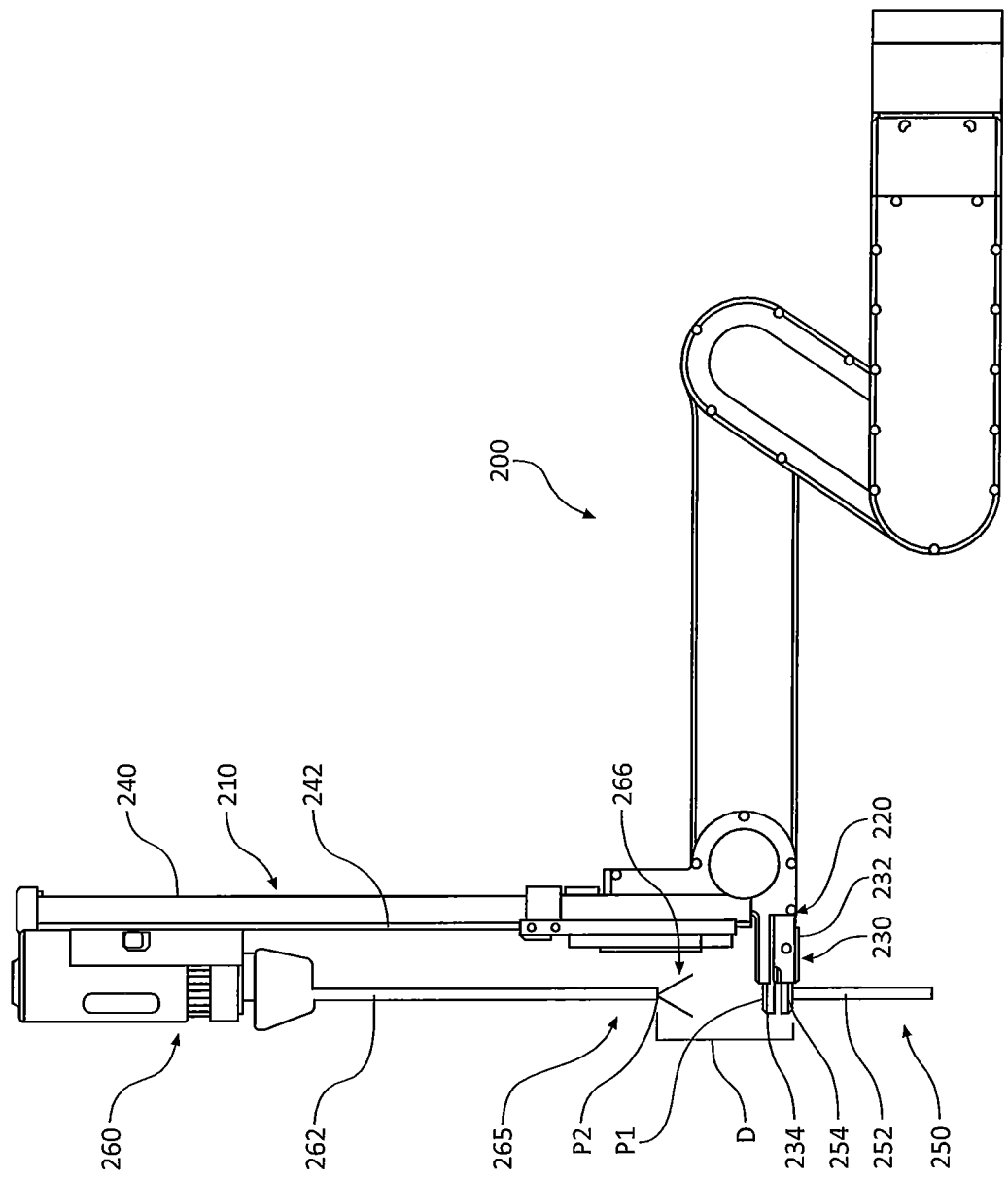
FIG. 2 is a side view of an arm that may be included in the robotic surgical system of FIG. 1 in an open position.

Turning now to FIG. 2, a side view is provided of a robotic arm 200 (similar to robotic arms 2, 3) including a mounting assembly 210 for securing surgical tools thereto. The robotic arm 200 is made up of three members connected via joints. The mounting assembly 210 is coupled to a distal end 220 of the arm 200 and includes a mounting device 230 and a longitudinally-extending support 240. The mounting device 230 is made up of a housing 232 which supports a clamping and release assembly 234 and is configured to selectively secure a variety of surgical tools therein to thereby secure a surgical tool to the robotic arm. Although the mounting device 230 may be adapted to receive a variety of surgical tools, the mounting device 230 receives a trocar 250, in an embodiment, as will be discussed in detail herein. The trocar 250 is releasably secured within the mounting device 230 through a transition between an open configuration and a closed configuration of the clamping assembly 234. The trocar 250 includes a cannula 252 configured to provide a pathway to a surgical site within the patient and has an access port 254 for receiving an end effector 265 of an instrument 260, which may perform the surgical operation on the patient. In an example, the end effector 265 includes a jaw assembly 266.

The longitudinally-extending support 240 extends substantially perpendicularly relative to the housing 232 of the mounting device 230 and supports a vertical rail 242. The vertical rail 242 is coupled to the support 240 and extends along a length of the support 240. The vertical rail 242 is configured such that an instrument 260 may be slideably coupled thereto and aligned with the trocar 250. In particular, the jaw assembly 266 extending from a rod or shaft 262 of the instrument 260 is substantially aligned with the trocar 250 so that it can be inserted into or removed from the access port 254 of the trocar 250. According to an embodiment, the vertical rail 242 is configured for positioning the jaw assembly 266 of the instrument 260 at least between a position P1 located just prior to entry into the access port 254 and a position P2 located a distance from the access port 254.

Figure 3A:
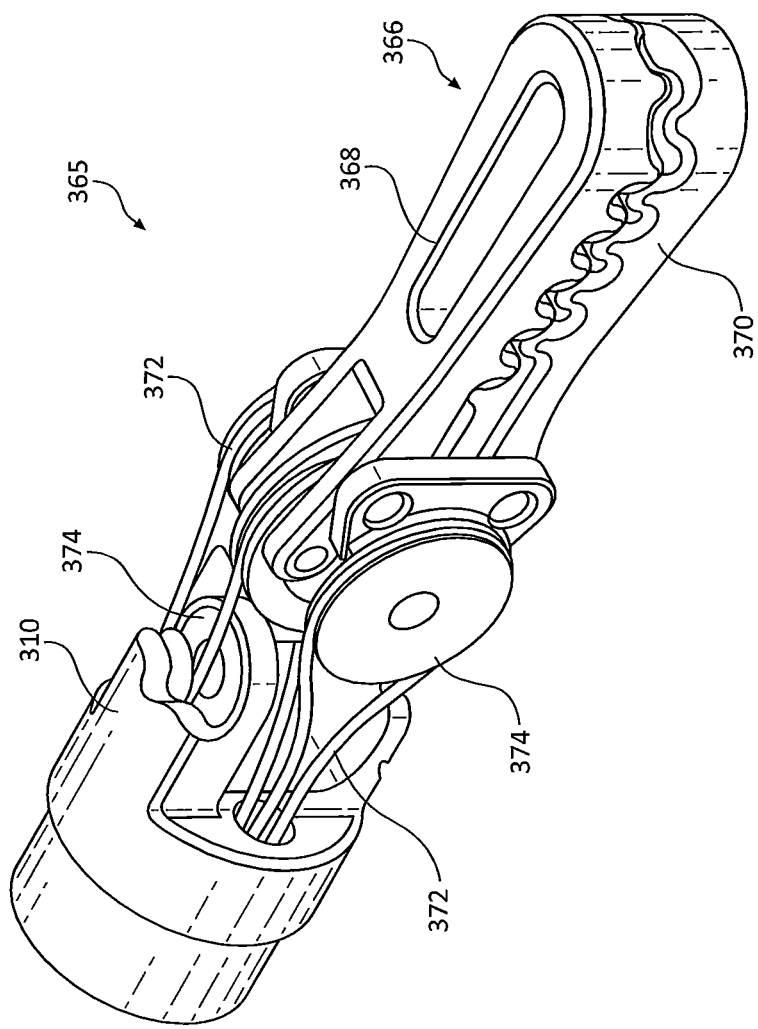
FIGS. 3A and 3B are perspective views of an end effector including a jaw assembly in a closed position and an open position, respectively, that may be implemented with the arm of FIG. 2.
Figure 3B:
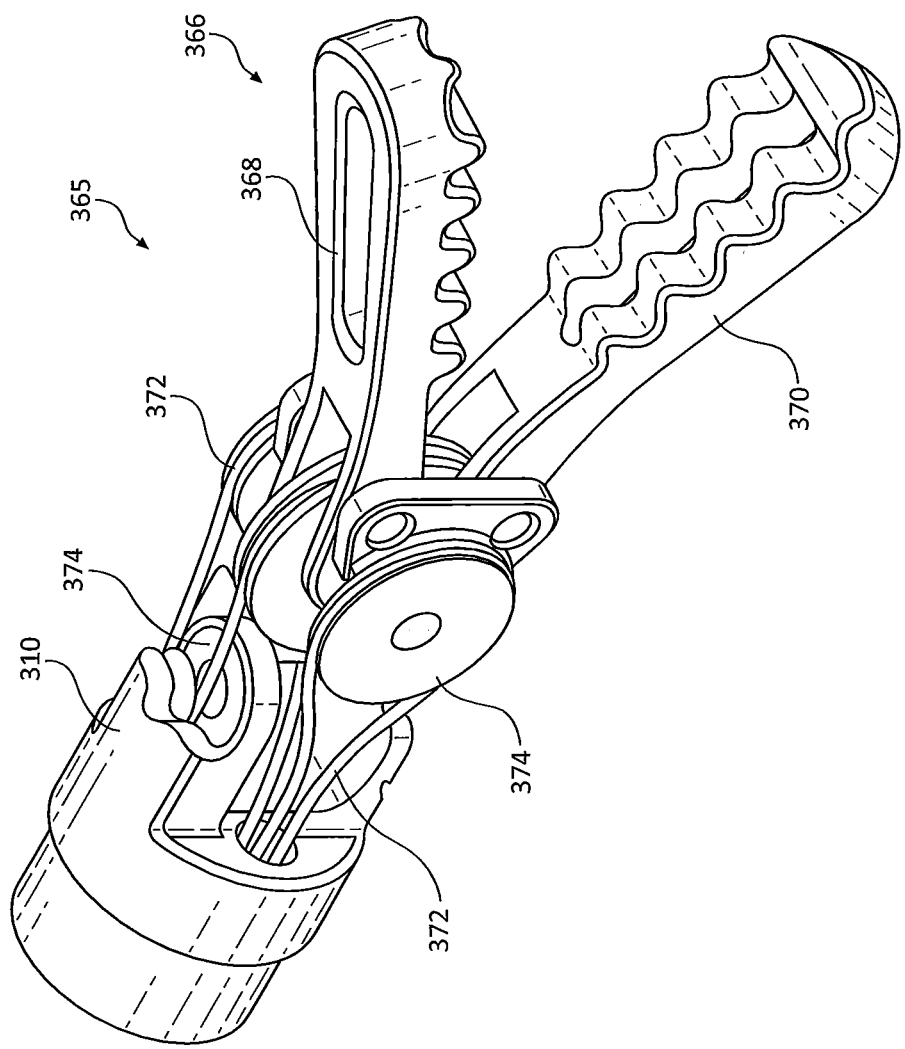

The jaw assembly 266 of the instrument 260 is configured to be movable between a closed position at least at position P1, for disposal within the cannula 252, and an open position, when located at least at position P2 and/or at a position external to the cannula 252. FIGS. 3A and 3B are perspective views of an end effector 365 including a jaw assembly 366 in a closed position and an open position, respectively. In addition to the jaw assembly 366, the end effector 365 includes a wrist assembly 310, to which the jaw assembly 366 is pivotally connected. The jaw assembly 366 includes a pair of jaws 368, 370 that can be manipulated using cables 372 that are coupled to pulley 374 for opening and closing the jaws 368, 370. In other embodiments, the instrument 260 may be forceps, scissor cutting tools, pliers, staplers, electrosurgical forceps or other tools including jaws or similar components for grasping.

Figure 4:
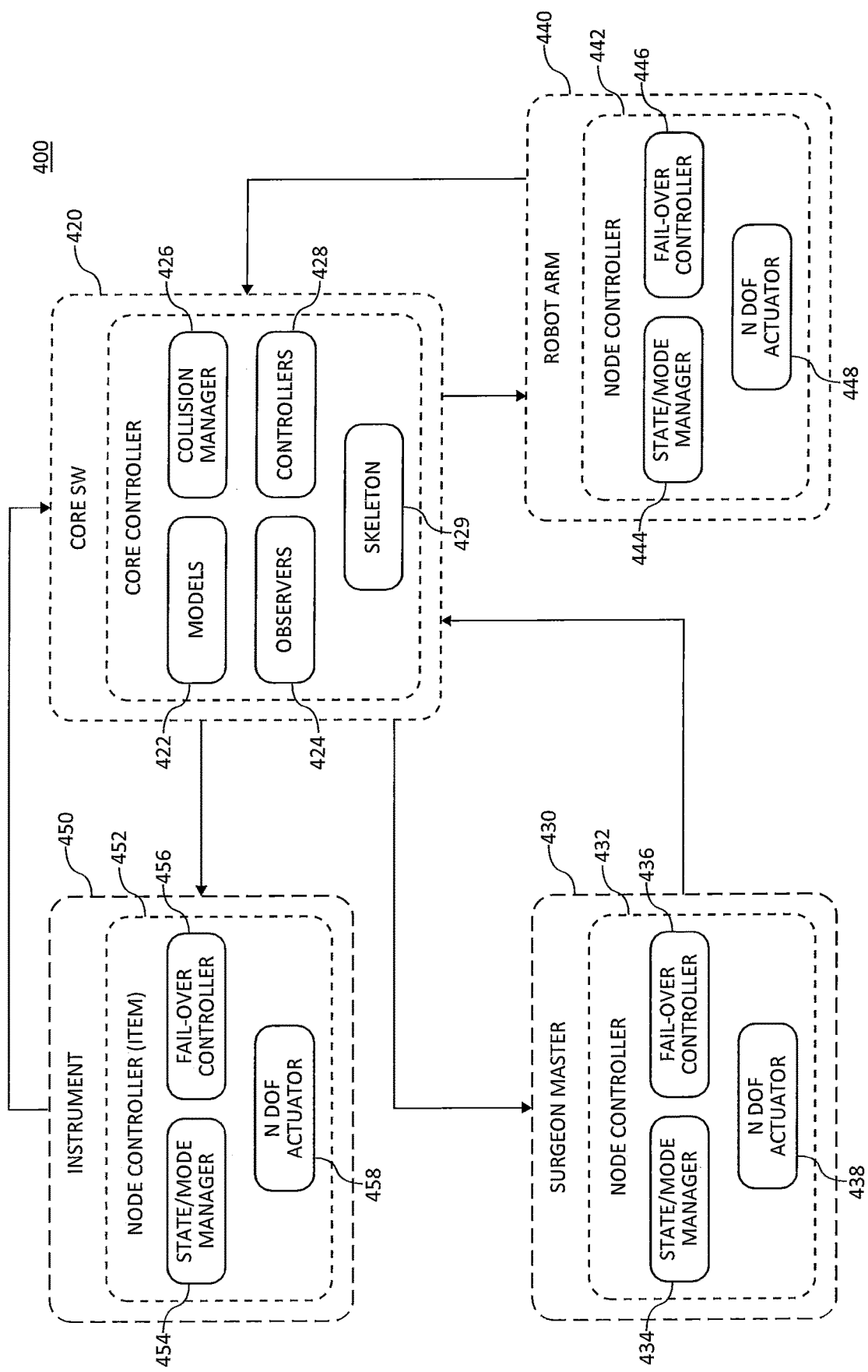
FIG. 4 is a block diagram of control components, of the present disclosure, for controlling the robotic surgical system of FIG. 1.

A simplified functional block diagram of a system architecture 400 of the robotic surgical system 10 is included in FIG. 4. The system architecture 400 includes a core module 420, a surgeon master module 430, a robot arm module 440, and an instrument module 450. The core module 420 serves as a central controller for the robotic surgical system 1 and coordinates operations of all of the other modules 430, 440, 450. For example, the core module 420 maps control devices to the arms 2, 3, 200, determines current status, performs all kinematics and frame transformations, and relays resulting movement commands. In this regard, the core module 420 receives and analyzes data from each of the other modules 430, 440, 450 in order to provide instructions or commands to the other modules 430, 440, 450 for execution within the robotic surgical system 1. Although depicted as separate modules, one or more of the modules 420, 430, 440, and 450 are a single component in other embodiments.

The core module 420 includes models 422, observers 424, a collision manager 426, controllers 428, and a skeleton 429. The models 422 include units that provide abstracted representations (base classes) for controlled components, such as the motors (for example, Motor 1 . . . n) and/or the arms 2, 3, 200. The observers 424 create state estimates based on input and output signals received from the other modules 430, 440, 450. The collision manager 426 prevents collisions between components that have been registered within the system 10. The skeleton 429 tracks the system 10 from a kinematic and dynamics point of view. For example, the kinematics item may be implemented either as forward or inverse kinematics, in an embodiment. The dynamics item may be implemented as algorithms used to model dynamics of the system's components.

The surgeon master module 430 communicates with surgeon control devices at the console 5 and relays inputs received from the console 5 to the core module 420. In accordance with an embodiment, the surgeon master module 430 communicates button status and control device positions to the core module 420 and includes a node controller 432 that includes a state/mode manager 434, a fail-over controller 436, and a N degree of freedom ("DOF") actuator 438.

The robot arm module 440 coordinates operation of a robot arm subsystem, an arm cart subsystem, a set up arm, and an instrument subsystem in order to control movement of a corresponding arm 2, 3, 200. Although a single robot arm module 440 is included, it will be appreciated that the robot arm module 440 corresponds to and controls a single arm. As such, additional robot arm modules 440 are included in configurations in which the system 10 includes multiple arms 2, 3, 200. The robot arm module 440 includes a node controller 442, a state/mode manager 444, a fail-over controller 446, and a N degree of freedom ("DOF") actuator 348.

The instrument module 450 controls movement of the instrument 260 (shown in FIG. 2) attached to the arm 2, 3, 200. The instrument module 450 is configured to correspond to and control a single instrument. Thus, in configurations in which multiple instruments are included, additional instrument modules 450 are likewise included. In an embodiment, the instrument module 450 obtains and communicates data related to the position of the end effector or jaw assembly 266 (which may include the pitch and yaw angle of the jaws), the width of or the angle between the jaws 368, 370, and the position of the access port 254. The instrument module 450 has a node controller 452, a state/mode manager 454, a fail-over controller 456, and a N degree of freedom ("DOF") actuator 458.

The position data collected by the instrument module 450 is used by the core module 420 to determine when the instrument 260 is within the surgical site, within the cannula 252, adjacent to the access port 254, or above the access port 254 in free space. The core module 420 determines whether to provide instructions to open or close the jaws of the instrument 260 based on the positioning of the instrument 260. For example, when the position of the instrument 260 indicates that the instrument 260 is within the cannula 252, instructions are provided to maintain the jaw assembly 266 in a closed position. When the position of the instrument 260 indicates that the instrument 260 is outside of the access port 254 (specifically, jaw assembly 266), instructions are provided to open the jaw assembly 266.

Figure 5:
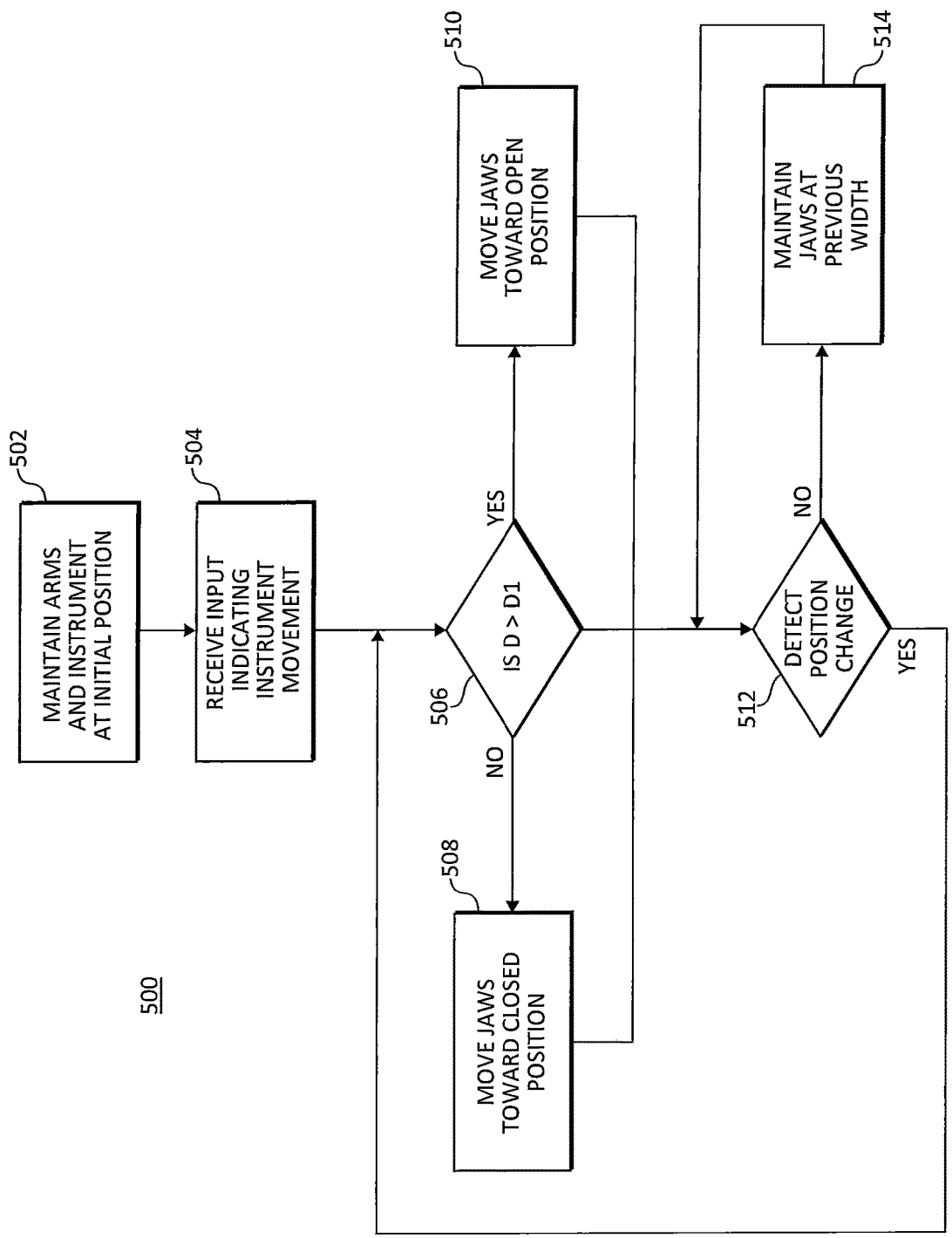
FIG. 5 is a flow diagram of a process for controlling the robotic surgical system of FIG. 1.
Figure 6:
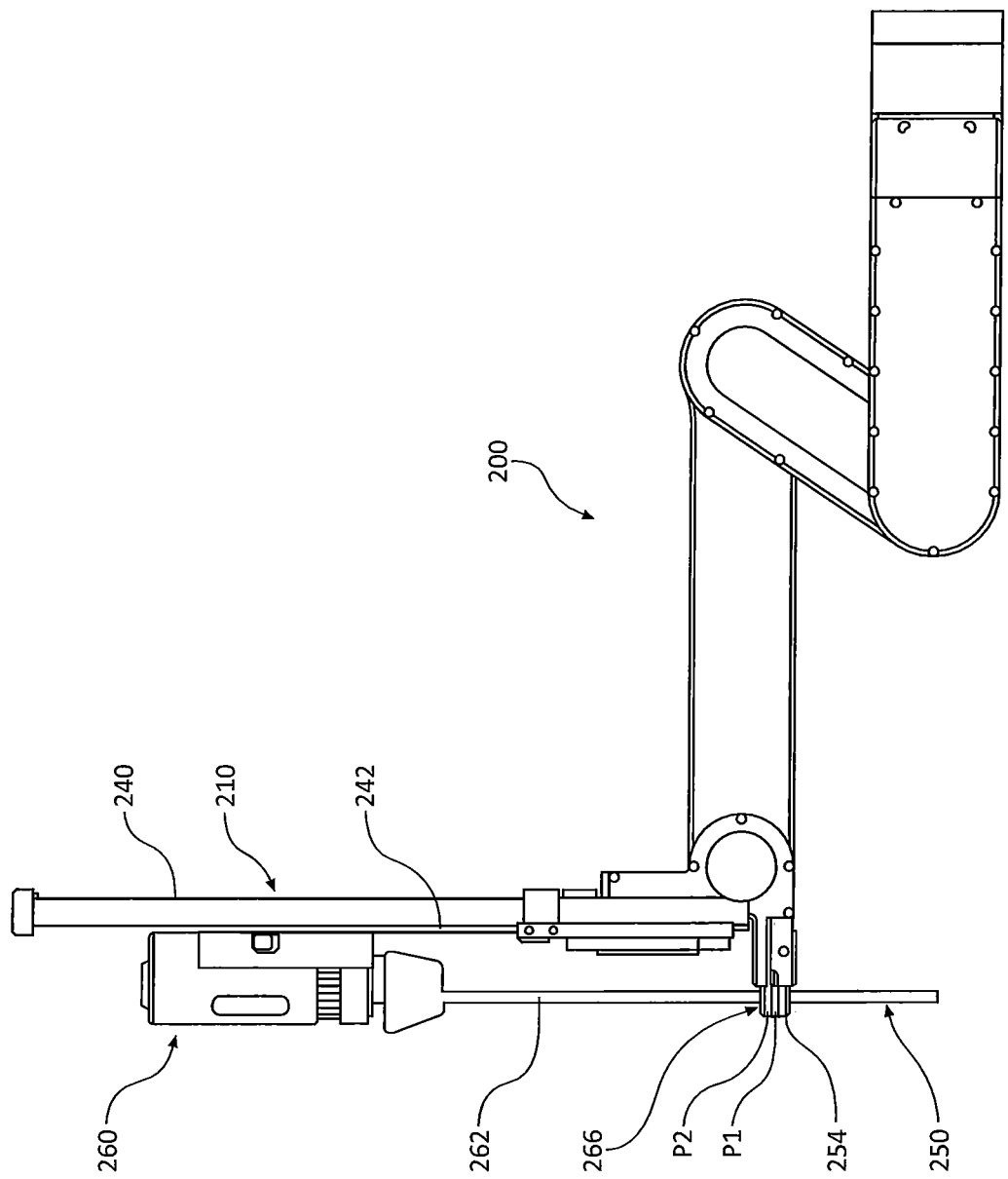
FIG. 6 is a side view of an arm that may be included in the robotic surgical system of FIG. 1 in a closed position.

FIG. 5 is a flow diagram of a method 400 of controlling the robotic surgical system 10, and in particular, the instrument 260 coupled to a corresponding arm 200, in accordance with an embodiment. With additional reference to FIG. 2, at system initialization, for example, during or at system start up, reset, or reboot, the arm 200 and instrument 260 are maintained at an initial position at step 510. In an embodiment, the initial position includes a distal end of the arm 200 being placed a predetermined height above the patient table 12 (FIG. 1) and the instrument 260 to be controlled being placed at a position proximal from the patient table 12. In particular, the instrument 260 is positioned along the vertical rail 242 such that the jaw assembly 266 of the instrument 260 is located outside of the cannula 252. For example, as shown in FIG. 2, the jaw assembly 266 may be located at position P2 a distance D away from the position P1 of the access port 254. It will be appreciated that P2 may be located at a location different than that depicted in FIG. 2 in other embodiments, and distance D corresponds to any distance between P1 and P2. Additionally, although referenced herein generally as the distance between P1 and P2, distance D is a vertical distance between position P1 and position P2, in another embodiment. In accordance with another embodiment, distance D is a horizontal distance between position P1 and position P2.

The jaws 368, 370 of the jaw assembly 266 are either moved to or maintained in an open position. In accordance with an embodiment in which the jaw assembly 266 is configured as a hinge joint, the open position includes the jaws 368, 370 having an angle therebetween of greater than about 0 to about 10 degrees. In another embodiment, a maximum angle between the jaws 368, 370 is about 45 degrees. In an embodiment in which the jaw assembly 266 is configured as a clamp, the jaws 368, 370 are movable between an open position and a closed position, wherein a maximum predetermined width between the jaws 368, 370 is in a range of between about 4 millimeters (mm) to about 25 mm, in an embodiment. In still another embodiment, the jaws 368, 370 may be configured to move (e.g., closer and further away from each other) in two parallel planes relative to one another. Alternatively, the predetermined width between the jaws 368, 370 is greater or less than the aforementioned range.

Next, an input is received by the system 10 indicating movement of the instrument 260 in a direction co-axial with the access port at step 504. Determination of a position of the instrument 260 may be determined, for example, by a Z-slide encoder, by detecting distance between sensors disposed on an end of the vertical rail 242 and the instrument 260, by contact sensors such as a proximity switch, by contactless configurations such as a laser beam that is interrupted by the instrument 260 and the like. In response to an input received by the system 10 indicating a movement of the instrument 260 along the direction co-axial with the access port, a determination is made as to whether the distance D between the position of the jaw assembly 266 of the instrument 260 at P2 relative to the position of the access port 254 at P1 is greater than a predetermined distance D1 at 506. The predetermined distance D1 is a threshold value at which the jaws 368, 370 open or close. In an embodiment, the predetermined distance D1 is a value in a range of between about 10 mm and about 25 mm. In another embodiment, the predetermined distance D1 is a value that is greater or less than the aforementioned range. The predetermined distance D1 may be customized by type of instrument and/or or by end-effector and may be stored in the memory 14, a portion of which may be associated with or located on the arm 200 or on the instrument 260.

The input is received from the console 5. For example, the clinician may press a physical button or virtual button on a touch screen at the console 5. In another embodiment, the input is received at the arm 200. For instance, a technician in the proximity of the patient table 12 manipulates the vertical rail 242, either by pulling the vertical rail 242 closer to the access port 254 or pushing the vertical rail 242 away from the access port 254.

If the determination is made that the distance D between the position of the jaw assembly 266 of the instrument 260 at P2 relative to the position of the access port 254 at P1 is not greater than the predetermined distance "D1" as shown in FIG. 5, then instructions are provided to the instrument module 450 to move the jaws 368, 370 toward the closed position at step 508. If the determination is made that the distance D between the position of the jaw assembly 266 of the instrument 260 at P2 relative to the position of the access port 254 at P1 is greater than the predetermined distance "D1," then instructions are provided to the instrument module 450 to move the jaws 368, 370 of the instrument 260 toward the open position at step 510.

According to an embodiment, the amount of closure of the jaws 368, 370 is based in part on the distance D of the jaw assembly 266 from the access port 254. In an embodiment, the jaws 368, 370 are substantially closed (e.g., positioned such that the jaws 368, 370 have a width that is less than the diameter of the access port 254) when the position of the jaw assembly 266 at P2 is located at or adjacent P1. In another embodiment, the jaws 368, 370 remain in the substantially closed position while located within a predetermined range of distances of the access port 254 to define a buffer zone in the space outside of the cannula 252.

As the jaw assembly 266 moves further away from the access port 254 or outside the buffer zone, the jaws 368, 370 gradually become wider until a maximum width is obtained. In an embodiment, the core module 420 includes a look-up table or algorithm for interpolation of jaw width values from the substantially closed position to the maximum open position based on the distance of the jaw assembly 266 from the access port 254 or outside the buffer zone and provides instruction to the instrument module 450 to open the jaws 368, 370 to a desired width. According to an embodiment, the jaw width is directly proportional to the distance of the jaw assembly 266 from the access port 254 or outside the buffer zone. In another embodiment, the jaw width is relatively small when closest to the access port 254 or buffer zone and a percentage of increase in jaw width is greater the further away from the access port 254 or buffer zone the jaw assembly 266 is positioned. In still another embodiment, the core module 420 includes a look-up table or algorithm for interpolation of jaw angle values from the substantially closed position to the maximum open position based on the distance of the jaw assembly 266 from the access port 254 or outside the buffer zone and provides instruction to the instrument module 450 to open the jaws 368, 370 to a desired angle. In any case, when the jaws 368, 370 obtain the maximum width or angle therebetween, the jaws 368, 370 are maintained at the maximum width or angle as long as the jaw assembly 266 is located at a position beyond that at which the maximum width or angle is triggered and hence, located a distance greater than a maximum distance from the access port 254.

Closure of the jaws 368, 370 operates in a similar manner as the above-detailed opening sequence. For example, the distance between the jaws 368, 370 gradually becomes narrower until a minimum width (or substantial closure) is obtained. In an embodiment, the core module 420 uses the look-up table or algorithm for interpolation of jaw width values from the maximum open position to the substantially closed position based on the distance of the jaw assembly 266 from the access port 254 or outside the buffer zone and provides instruction to the instrument module 450 to close the jaws 368, 370 a desired width. According to an embodiment, the jaw width is directly proportional to the distance of the jaw assembly 266 from the access port 254 or outside the buffer zone. In another embodiment, the core module 420 includes a look-up table or algorithm for interpolation of jaw angle values from the maximum open position to the substantially closed position based on the distance of the jaw assembly 266 from the access port 254 or outside the buffer zone and provides instruction to the instrument module 450 to close the jaws 368, 370 to a desired angle. For instance, in a configuration in which at a maximum width the jaws 368, 370 are at a 45 degree angle, if the jaw assembly 266 is located half-way between position P1 and position P2, the jaws 368, 370 would be open to a 22.5 degree angle. In another embodiment, the jaw width is relatively small when closest to the access port 254 or buffer zone and a percentage of increase in jaw width is greater the further away from the access port 254 or buffer zone the jaw assembly 266 is positioned. Thus, in an embodiment, the width of the jaws 368, 370 decreases more rapidly the further away from the access port 254 or buffer zone. When the jaws 368, 370 obtain the minimum width or angle therebetween, the jaws 368, 370 are maintained at the minimum width (or substantially closed) as long as they are located at a position within which the minimum width or angle is triggered and hence, located a minimum distance from the access port 254. In still another embodiment, the jaws 368, 370 close immediately based on the distance of the jaw assembly 266 from the access port 254 or outside the buffer zone where instructions to do so are included in the instrument module 450 for closure of the jaws 368, 370 to a desired width, rather than in a gradual manner.

In any case, a determination is made as to whether the position of the jaw assembly 266 (P2) has changed relative to the position of the access port 254 (P1) at step 512. For example, the core module 420 provides instructions to the instrument module 450 to detect a position change of the jaw assembly 266 relative to the access port 254. If a position change of the jaw assembly 266 is detected, the method iterates at step 506. If not, the jaws 368, 370 are maintained at the previous width or angle.

As briefly noted above, input into the system 10 to re-position the jaw assembly 266 relative to the access port 254 may be received by the bedside technician. By implementing the above-described process, the technician can manually move the location of the jaw assembly 266 along the vertical rail 242 to thereby cause the jaws 368, 370 to open or close. The manual movement may occur by physically pushing or pulling the vertical rail 242 along the longitudinally-extending support or by using a button (physical or virtual) to activate an actuation system configured to position the vertical rail 242.

In an embodiment, in order to improve safety during use of the system 10, the core module 420 is configured to prioritize input received at the instrument 260 (for example, the re-positioning of the vertical rail 242, manual opening or closing of the jaws 368, 370 either by manually manipulating the jaws 368, 370 or by pressing a physical or virtual button for opening or closing the jaws 368, 370) over inputs received from the console 5.

In accordance with another embodiment, although described as including vertical rail 242, other robotic arm designs omit the vertical rail 242 and, instead, include additional components for translating the instrument 260 in the x-, y-, and z-directions, ultimately aligning the instrument 260 concentric with the access port 254. In such a configuration, software-enforced kinematics are implemented into the robot arm module 440 that instruct the robotic arm and corresponding instrument to translate concentric to the access port, through coordination of the other joints (similar to a human arm) during surgeon-controlled motions. Instructions are also included for responding to manual movement by the technician, which activate a mode where the system allows the technician to translate the arm along the z-direction (or other directions), while motors associated with the arm resists motion that deviates from one or more of the x-, y-, or z-directions.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of manipulating an end effector of a surgical instrument coupled to an arm of a robotic surgical system, the method comprising:
    detecting a position of the end effector relative to an instrument access port; and
    electromechanically manipulating the end effector to a position that does not clear an opening of the access port responsive to the detected position of the end effector clearing the opening of the access port.

2. A method of manipulating jaws of a surgical instrument coupled to an arm of a robotic surgical system, the method comprising:
    detecting a position of the surgical instrument relative to an instrument access port of a trocar; and
    electromechanically opening the jaws of the surgical instrument in response to a determination that a distance between the jaws of the surgical instrument and the access port of the trocar is greater than a predetermined distance.

3. The method of claim 2, wherein the opening of the jaws of the surgical instrument includes:
    increasing a distance between the jaws of the surgical instrument, in response to a determination that the distance between the position of the surgical instrument and the position of the access port of the trocar is increasing.

4. The method of claim 3, wherein the opening of the jaws of the surgical instrument includes gradually increasing the distance between the jaws proportionally based on an interpolation of the distance between the position of the jaws of the surgical instrument relative to the position of the access port of the trocar as the distance between the position of the surgical instrument relative to the position of the access port of the trocar increases.

5. The method of claim 2, further comprising:
    closing the jaws of the surgical instrument in response to a determination that the distance between the position of the surgical instrument and the position of the access port of the trocar is less than the predetermined distance.

6. The method of claim 5, wherein the closing of the jaws of the surgical instrument includes gradually decreasing the distance between the jaws proportionally based on an interpolation of the distance between the position of the surgical instrument relative to the position of the access port of the trocar as the distance between the position of the surgical instrument relative to the position of the access port of the trocar decreases.

7. The method of claim 2, wherein:
the surgical instrument is moveable in a direction co-axial with the access port of the trocar; and
the opening of the jaws of the instrument includes increasing a distance between the jaws, based on an interpolation of a height of the surgical instrument along the direction co-axial with the access port of the trocar to the position of the access port of the trocar.

8. The method of claim 2, wherein the distance includes a predefined range of distances and maintaining the jaws of the surgical instrument in a closed position, in response to a determination that the distance between the position of the surgical instrument and a position of the access port of the trocar is within the predefined range of distances.

9. The method of claim 2, wherein the surgical instrument defines a longitudinal instrument axis, and wherein the access port of the trocar defines a longitudinal trocar axis, wherein the method comprises:
moving the surgical instrument along the longitudinal trocar axis while the longitudinal instrument axis is co-axial therewith; and
the opening of the jaws of the instrument includes increasing a distance between the jaws, based on an interpolation of a height of the surgical instrument along the direction co-axial with the access port of the trocar to the position of the access port of the trocar.

* * * * *